US 6,662,117 B2

United States Patent
Naito

(10) Patent No.: US 6,662,117 B2
(45) Date of Patent: Dec. 9, 2003

(54) PARTICLE ANALYZER AND PARTICLE CLASSIFYING METHOD

(75) Inventor: Takamichi Naito, Kobe (JP)

(73) Assignee: Sysmex Corporation, Hyogo (JP)

( * ) Notice: Subject to any disclaimer, the term of this patent is extended or adjusted under 35 U.S.C. 154(b) by 211 days.

(21) Appl. No.: 09/910,878

(22) Filed: Jul. 24, 2001

(65) Prior Publication Data

US 2002/0040277 A1 Apr. 4, 2002

(30) Foreign Application Priority Data

Jul. 24, 2000 (JP) .................................. 2000-222511
Jun. 27, 2001 (JP) .................................. 2001-194838

(51) Int. Cl.⁷ ............................................. G06K 9/00
(52) U.S. Cl. ........................ 702/29; 702/30; 702/31; 702/32; 702/45
(58) Field of Search ........................... 702/29, 30, 31, 702/32, 45, FOR 116, FOR 127–128, FOR 140; 382/128, 133, 134; 356/39, 73, 108; 436/63

(56) References Cited

U.S. PATENT DOCUMENTS

| 4,661,913 | A | * | 4/1987 | Wu et al. ..................... 702/19 |
| 5,125,737 | A | * | 6/1992 | Rodriguez et al. ........... 359/39 |
| 5,448,349 | A | * | 9/1995 | Kosaka ......................... 356/73 |
| 5,532,943 | A | * | 7/1996 | Asano et al. ................. 702/21 |
| 5,690,105 | A | * | 11/1997 | Shibata et al. .............. 600/300 |
| 5,703,959 | A | * | 12/1997 | Asano et al. ............... 382/133 |
| 5,721,433 | A | * | 2/1998 | Kosaka ....................... 250/573 |
| 5,731,867 | A | * | 3/1998 | Katayama .................... 356/73 |
| 5,812,419 | A | * | 9/1998 | Chupp et al. ................ 702/20 |
| 5,824,269 | A | * | 10/1998 | Kosaka et al. ............... 422/73 |
| 5,831,723 | A | * | 11/1998 | Kubota et al. ............... 356/73 |
| 5,939,326 | A | * | 8/1999 | Chupp et al. ................ 436/43 |
| 6,181,319 | B1 | * | 1/2001 | Fujita et al. ............. 345/440.1 |
| 6,246,786 | B1 | * | 6/2001 | Nishikiori et al. ......... 382/134 |

FOREIGN PATENT DOCUMENTS

JP         05-149863         6/1993

* cited by examiner

Primary Examiner—Marc S. Hoff
Assistant Examiner—Carol S Tsai
(74) Attorney, Agent, or Firm—Birch, Stewart, Kolasch, & Birch, LLP

(57) ABSTRACT

A particle analyzer includes a detecting section for detecting at least two kinds of parameters from a plurality of particles included in a sample, the two kinds of parameters representing characteristics of each particle, a processing section for processing the parameters detected by the detecting section; and an output section for outputting a result processed by the processing section, wherein the processing section includes a distribution chart creating section for creating a scattergram of the particles based on the detected parameters, a region presetting section for presetting a particle distribution region in the created scattergram, and a classifying section for calculating a classifying line corresponding to a particle distribution state in the preset particle distribution region and for classifying the particles on the scattergram by the calculated classifying line.

10 Claims, 11 Drawing Sheets

PARTICLE ANALYZER AND PARTICLE CLASSIFYING METHOD

CROSS-REFERENCE TO RELATED APPLICATION

This application is related to Japanese Patent Applications Nos. 2000-222511 filed in Jul. 24, 2000 and 2001-194838 filed in Jun. 27, 2001, whose priorities are claimed under 35 USC §119, the disclosures of which are incorporated by reference in their entirety.

BACKGROUND OF THE INVENTION

1. Field of the Invention

The present invention relates to a particle analyzer for classifying particles (for example, blood cells) in a liquid sample and measuring and analyzing the number and characteristics thereof.

2. Description of the Related Art

A conventional particle analyzer serves to electrically or optically measure parameters representing characteristics of particles in a blood sample such as erythrocytes, leukocytes or blood platelets, to create a two-dimensional scattergram based on the parameters thus obtained and to classify the particles and count the number of the classified particles. There have been known various methods of carrying out the classification on the assumption that the particles on the scattergram are normally distributed in all directions to form a cluster. For example, Japanese Unexamined Patent Publication No. Hei 5(1993)-149863 has disclosed a method of setting a fixed region in which particles belonging to a cluster will inevitably appear based on previously obtained information, obtaining an initial center-of-gravity position in the fixed region and calculating a degree of reversion to the cluster of each particle outside the fixed region and a weighted center-of-gravity position, thereby determining whether the particle belongs to the cluster. In this method, the particles close to two clusters can be allocated to each cluster. In case the separation between the clusters is poor, therefore, this method is effective. Moreover, the position of a center of gravity of each cluster and the spread of distribution are calculated. Therefore, it is also possible to detect a cluster having an abnormal pattern.

However, some kinds of particles are not always distributed normally in all directions to form a cluster. For example, a certain kind of cells sometimes have a larger size than a general size thereof although such cells have a low frequency. In such a case, there is such a distribution that most of the particles are collected in the vicinity of the center of gravity of the cluster, while the remaining particles are distributed in a position which is very far from the center of gravity in a specific direction. An example is shown in FIG. 14. FIG. 14 shows a state in which a certain kind of particles are distributed over the scattergram. It is apparent that most of the particles are distributed in the vicinity of a center G of gravity in FIG. 14, while the remaining particles are spread in the upward right direction of the center of gravity. If this kind of particles are classified by a conventional method, the cluster region should be expanded into a region in which the particles are not present. Consequently, it is hard to accurately determine the cluster.

Moreover, one of the two parameters creating a two-dimensional scattergram often fluctuates depending on the type of sample or a preservation condition of the sample. In this case, the conventional method calculates the position of the center of gravity of each cluster and the spread of distribution on the premise that an inclination of the distribution of each cluster is constant. Therefore, it is difficult to cope with a fluctuation in the inclination of the distribution of the cluster, and the accurate classification is hindered.

SUMMARY OF THE INVENTION

The present invention has been made in consideration of such circumstances and has an object to provide a particle analyzer capable of calculating a classifying line corresponding to a particle distribution state over a scattergram and counting, with high precision, particles which are not normally distributed, and a particle classifying method thereof.

The present invention provides a particle analyzer comprising a detecting section for detecting at least two kinds of parameters from a plurality of particles included in a sample, the two kinds of parameters representing characteristics of each particle, a processing section for processing the parameters detected by the detecting section; and an output section for outputting a result processed by the processing section, wherein the processing section includes a distribution chart creating section for creating a scattergram of the particles based on the detected parameters, a region setting section for presetting a particle distribution region in the created scattergram, and a classifying section for calculating a classifying line corresponding to a particle distribution state in the preset particle distribution region and for classifying the particles on the scattergram by the calculated classifying line.

Moreover, the present invention provides a particle classifying method which is carried out by the above analyzer, the method comprising the steps of detecting at least two kinds of parameters from a plurality of particles included in a sample, the two kinds of parameters representing characteristics of each particle, creating a scattergram based on the detected parameters, obtaining a variance-covariance matrix $\Sigma$ of the particles distributed in a predetermined particle distribution region in the scattergram and an eigenvector of $\Sigma$ and an eigenvalue of $\Sigma$, calculating a classifying line from the eigenvector and eigenvalue of $\Sigma$, and classifying the particles on the scattergram by the calculated classifying line.

DESCRIPTION OF THE PREFERRED EMBODIMENTS

A particle analyzer of the present invention includes a detecting section for detecting at least two kinds of parameters from a plurality of particles included in a sample, the two kinds of parameters representing characteristics of each particle, a processing section for processing the parameters detected by the detecting section, and an output section for outputting a result processed by the processing section, wherein the processing section includes a distribution chart creating section for creating a scattergram of the particles based on the detected parameters, a region setting section for presetting a particle distribution region in the created scattergram, and a classifying section for calculating a classifying line corresponding to a particle distribution state in the preset particle distribution region and for classifying the particles on the scattergram by the calculated classifying line.

The particle to be analyzed in the present invention is a substance contained in a body fluid such as blood or urine of a mammal including a human. The substance includes a cell such as an erythrocyte or a leukocyte.

For the detecting section for detecting the parameters representing the characteristics of the particle, it is possible to use a well-known device such as an optical detecting device for causing a liquid sample containing object particles to flow to a sheath flow cell to irradiate light and for detecting, as a characteristic parameter, a light signal such as transmitted light, scattering light or fluorescence, or an electric detecting device for causing the liquid sample containing the object particles to pass through an orifice and detecting, as a characteristic parameter, a change generated across the orifice in an electric resistance or an impedance.

Moreover, the processing section for processing the detected parameters may be constituted by a microcomputer or a personal computer. The output section for outputting a result processed by the processing section may include a display unit such as a CRT or an LCD or a printer such as a laser printer.

The scattergram to be created by the distribution chart creating section of the processing section may be a frequency distribution chart in which a frequency of the detected particles is represented on two-dimensional coordinates created based on two kinds of parameters.

Moreover, the particle distribution region preset in the scattergram through the region setting section is a fixed region to be supposed that an object kind of particles are always distributed, and is set to be a polygon region, for example.

Figure 14:
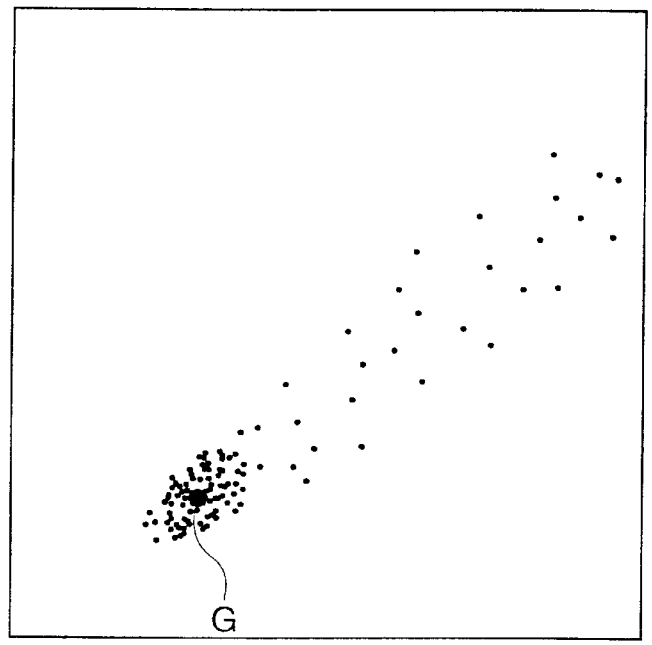
FIG. 14 is a chart showing an example of a state in which particles are distributed on a scattergram.
Figure 15:
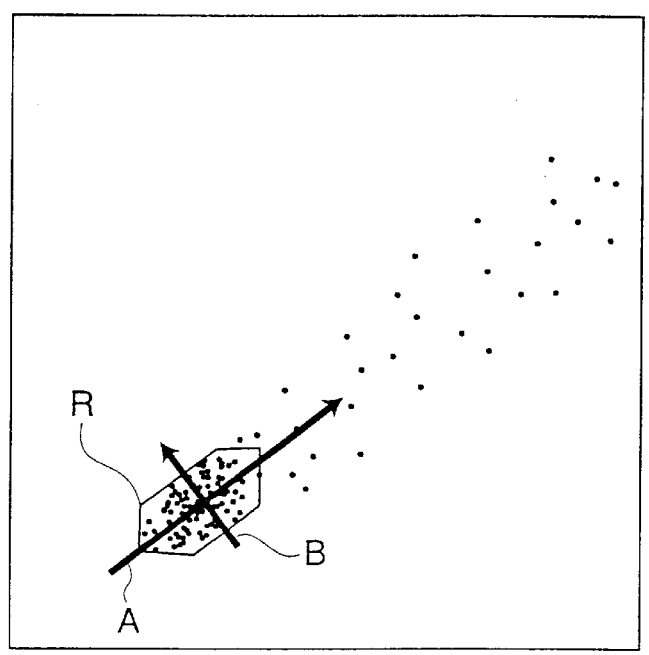
FIG. 15 is a chart showing the classifying method according to the embodiment of the present invention.

The classifying section serves to analyze a particle distribution state in a fixed particle distribution region set by the region setting section, thereby predicting a distribution state of the same kind of particles outside the fixed region, and to calculate a proper classifying line corresponding to the particle distribution state of the set particle distribution region. For example, it is possible to propose a method of analyzing a variance in a maximum variance direction of the particles in the set particle distribution region or in a direction orthogonal to the maximum variance direction. FIG. 15 shows a state in which a particle distribution region R is set in the distribution state of the particles illustrated in FIG. 14. Moreover, an arrow A shown in FIG. 15 indicates the maximum variance direction of a particle group distributed in the region R. Consequently, it is apparent that the particles outside the region R are distributed in the maximum variance direction. In other words, a direction (inclination) in which the particles to be classified are distributed over the scattergram can be predicted from the maximum variance direction in the predetermined particle distribution region. An arrow B in FIG. 15 indicates a direction orthogonal to the arrow A. By using a variance value in the direction (shown in the arrow B) orthogonal to the maximum variance direction of the particles in the predetermined particle distribution region, it is possible to predict a range in which the particles are distributed over the scattergram in the same direction.

More specifically, a variance-covariance matrix $\Sigma$ of the particles distributed in the predetermined particle distribution region may be obtained to calculate an eigenvector and an eigenvalue of $\Sigma$. On the premise that the scattergram constituted by the parameters is two-dimensional, two couples of eigenvectors and eigenvalues of $\Sigma$ are calculated. One of the eigenvectors corresponds to one of the eigenvalues. A direction of the eigenvector corresponding to a greater one of the two eigenvalues indicates the maximum variance direction of the particles distributed in the predetermined particle distribution region. The other eigenvector has a direction orthogonal to the eigenvector. The eigenvalue (indicating a variance) corresponding to the eigenvector can be an element for determining the distribution range of the particles in the direction orthogonal to the maximum variance direction.

Figure 16:
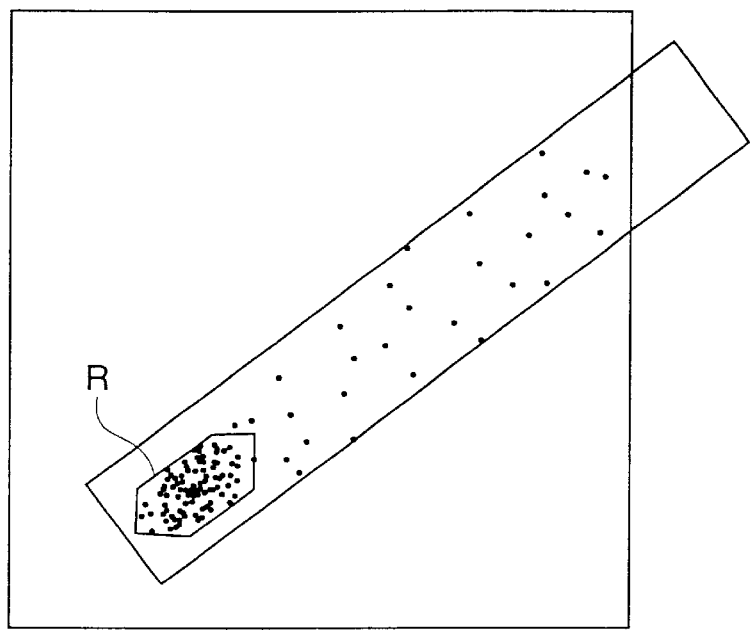
FIG. 16 is a chart showing the classifying method according to the embodiment of the present invention.

The classifying section according to the present invention calculates a classifying line to be drawn over the scattergram corresponding to the distribution state of the particles in the predetermined particle distribution region. The classifying line can take any manner, can be a straight line or a curve or can have any planar graphic. As shown in FIG. 16, for example, it is also possible to classify the particles on the scattergram through a rectangular classifying line. In this case, it is also possible to calculate the variance-covariance matrix $\Sigma$ of the particles distributed in the fixed region R, to set a direction of a greater one of the two eigenvector of $\Sigma$ thus obtained to be a longitudinal direction of the rectangle and to determine a length of a short side of the rectangle based on the eigenvalue of $\Sigma$ corresponding to the other eigenvector, thereby calculating the rectangular classifying line.

Figure 17:
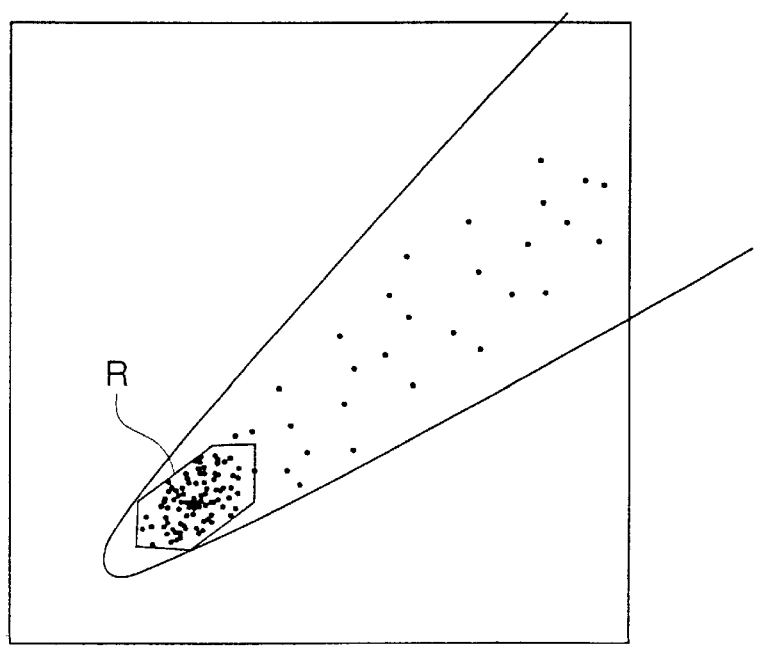
FIG. 17 is a chart showing the classifying method according to the embodiment of the present invention.

Alternatively, the classifying section according to the present invention may use a parabola for the classifying line as shown in FIG. 17. In this case, it is also possible to obtain the variance-covariance matrix $\Sigma$ of the particles distributed in the predetermined particle distribution region R, to regard a direction of a greater one of two eigenvectors of $\Sigma$ thus obtained as an inclination of an axis of the parabola and to regard an eigenvalue of $\Sigma$ corresponding to the other eigenvector as a degree of spread of the parabola, thereby calculating the parabola.

In the case in which the parabola is used for the classifying line as described above and the scattergram is represented on a x-y coordinates, the classifying section according to the present invention may calculate, as a classifying parabola, a parabola obtained by inclining a parabola of $y=ax^2 (a>0)$ in the maximum variance direction of the particles in the predetermined particle distribution region and translating the parabola on the coordinates so that a point of a minimum value of $y=ax^2$ is coincident with a point positioned apart in the maximum variance direction by n times as great as a standard deviation from a point of a most frequency value of the particles in the set particle distribution region and the parabola passes through a point positioned apart in a direction orthogonal to the maximum variance direction by n times as great as a standard deviation from the point of the most frequency value. Here, n indicates a numerical value set for fitting a particle group distributed on the scattergram with the parabola and is used for determining a final position of the parabola over the scattergram by translating the parabola having an inclination and a degree of spread determined. A specific numerical value to be substituted is appropriately determined depending on the type of particles to be analyzed or the like and, for example, 2.5 may be substituted. Moreover, the classifying section may further have a function of carrying out a coordinate transformation of the scattergram such that the classifying parabola is represented by $y=ax^2$ based on a relationship on the coordinates between $y=ax^2$ and the calculated classifying parabola.

The present invention will be described below in detail based on an embodiment shown in the drawings. The present invention is not restricted to the embodiment.

Figure 1:
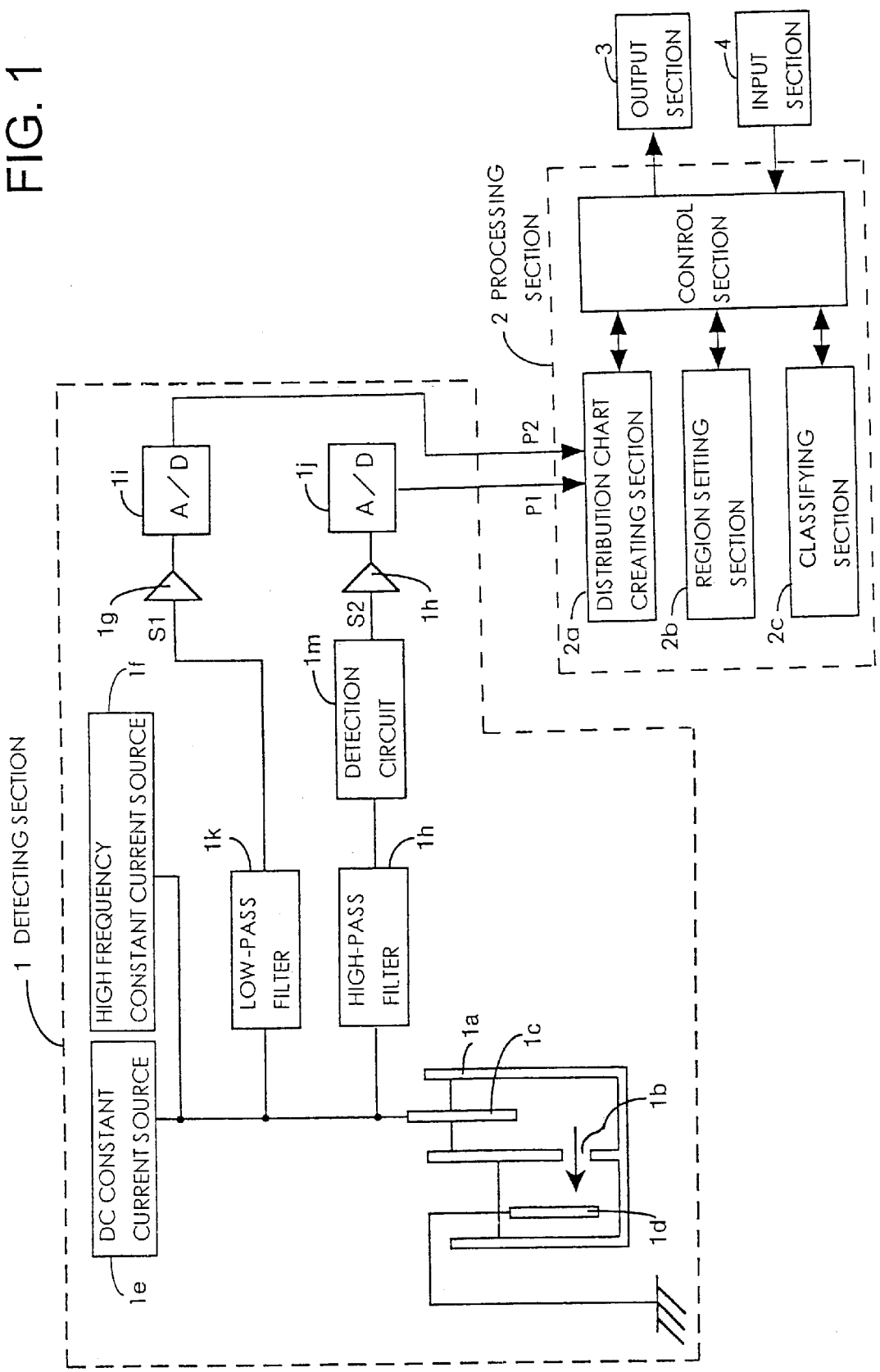
FIG. 1 is a block diagram showing an embodiment of the present invention.

In the present embodiment, the present invention is carried out in a blood analyzer. As shown in FIG. 1, the blood analyzer has a detecting section 1. The detecting section 1 serves to measure blood cells in a sample, i.e. a suspension subjected to a pretreatment such as addition of a diluent and a hemolytic agent for measurement. In the detecting section 1, each blood cell is measured and plural kinds of parameters are detected for each blood cell. The detecting section 1 serves to accommodate the suspension in a chamber 1a, to simultaneously supply a DC current and a high frequency current from a DC constant current source 1e and a high frequency constant current source 1f across a orifice 1b of the chamber 1a through electrodes 1c and 1d, to cause each blood cell to pass through the orifice 1b and to obtain a signal based on a change in resistance and a signal based on a change in impedance for each blood cell. When the DC current is caused to flow across the orifice 1b and one blood cell passes through the orifice 1b, a signal S1 proportional to the size of its cytoplasm is obtained.

Moreover, when the high frequency current is caused to flow across the orifice 1b, the impedance of a substance having a low density such a cytoplasm of the blood cell is reduced and the impedance of a substance having a high density such as a nucleus or a granule is increased. Therefore, a signal S2 integrating the density and size of the nucleus or granule of the blood cell passing through the orifice 1b is obtained. A low-pass filter 1k serves to remove a high frequency component in order to detect only a DC component from a voltage between the electrodes 1c and 1d and to obtain the signal S1. To the contrary, a high-pass filter 1n serves to remove the DC component from the voltage between the electrodes 1c and 1d and to obtain only an AC component. Moreover, a detection circuit 1m serves to detect the AC component of the voltage between the electrodes 1c and 1d to obtain the signal S2.

The signals S1 and S2 are amplified by amplifiers 1g and 1h and are then converted into digital signals representative of parameters P1 and P2 of by A/D converters 1i and 1j, and the parameters P1 and P2 are supplied to a processing section 2, respectively. The processing section 2 is constituted by a personal computer or a microcomputer, to which an output section 3 and an input section 4 are attached. A CRT is used for the output section 3 and a keyboard is used for the input section 4. The processing section 2 includes a distribution chart creating section 2a, a region setting section 2b, a classifying section 2c and a control section 2d. The control section 2d serves to control a processing in each of the distribution chart creating section 2a, the region setting section 2b and the classifying section 2c.

Figure 2:
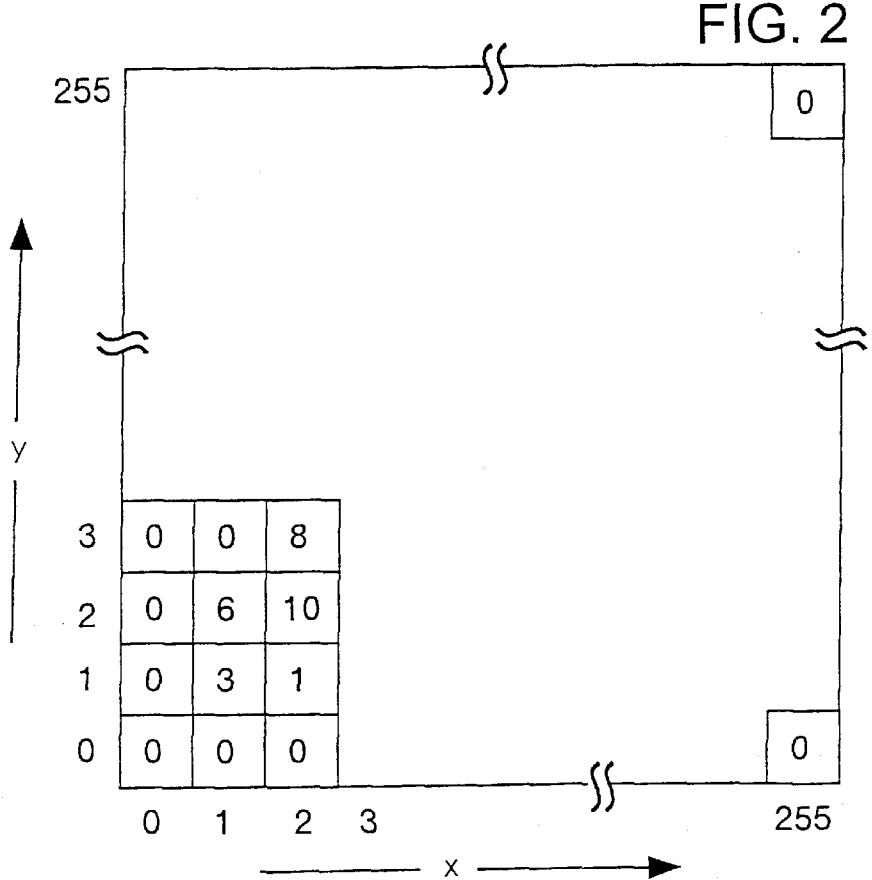
FIG. 2 is a distribution chart illustrating the embodiment of the present invention.

In the distribution chart creating section 2a, the parameter P1 representing the size of the cytoplasm of the blood corpuscle is classified into any of 256 channels from 0 to 255 (which will be hereinafter referred to as an i channel) and the parameter P2 integrating the density and size of the nucleus or the granule in the blood corpuscle is also classified into any of 256 channels from 0 to 255 (which will be hereinafter referred to as a j channel). Based on the parameters P1 and P2, a distribution chart of which x and y axes are graduated in the i and j channels is obtained as shown in FIG. 2.

Since each of the x and y axes has 256 channels, the distribution chart is constituted by 256×256 basic elements representing the state of blood cells in total. Each basic element stores the number of blood corpuscles corresponding thereto. As shown in FIG. 2, when a value of the basic element represented by channel 1 of the x axis and channel 2 of the y axis is six, the value represents that there are six blood cells of which parameter P1 and P2 are 1 and 2, respectively. The distribution chart created by the distribution chart creating section 2a is output as a two-dimensional scattergram shown in FIG. 3 through the output section 3.

Figure 3:
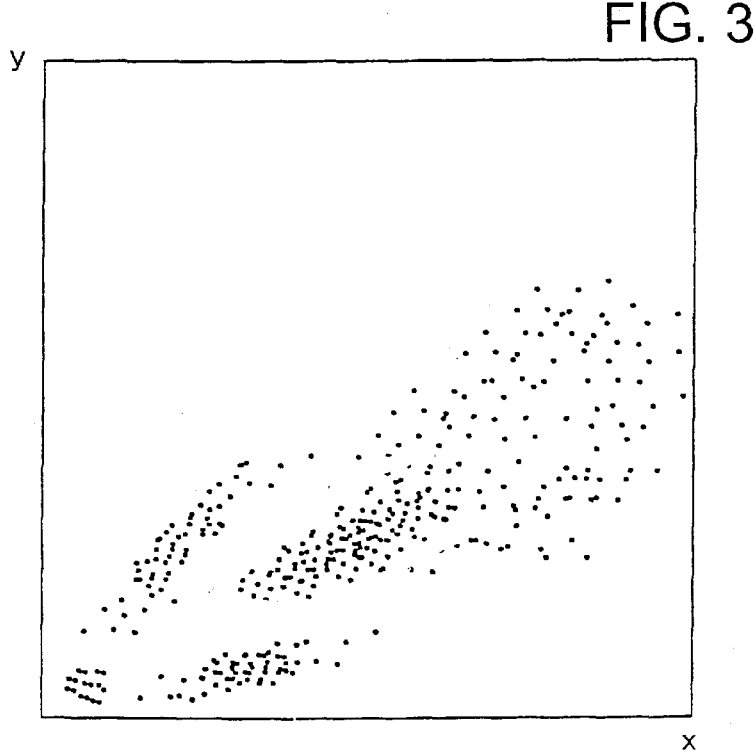
FIG. 3 is a scattergram showing the embodiment of the present invention.

An operation in such a structure will be described by taking, as an example, an analyzer for measuring immature leukocytes (which is mounted on XE-2100 produced by SYSMEX CORPORATION or the like). First of all, a controlled blood (of which cells and platelets have been artificially controlled) is diluted with a reagent for measuring immature cells. Thereby, erythrocytes are hemolyzed. In addition, cytoplasm of a leukocytes other than the immature cells is dissolved and reduced in size. Then, the diluted blood is accommodated in the chamber 1a of the device shown in FIG. 1. Thereafter a measurement is carried out. Consequently, a distribution chart and a two-dimensional scattergram corresponding to FIGS. 2 and 3 are obtained respectively (hereinafter description will be given by using only the two-dimensional scattergram for simplicity). The region setting section 2b presets, in the scattergram shown in FIG. 4, a particle distribution region (hereinafter referred to as a "fixed region" for convenience) R1 (hexagon) in which immature granules in the controlled blood should be inherently present.

Figure 5:
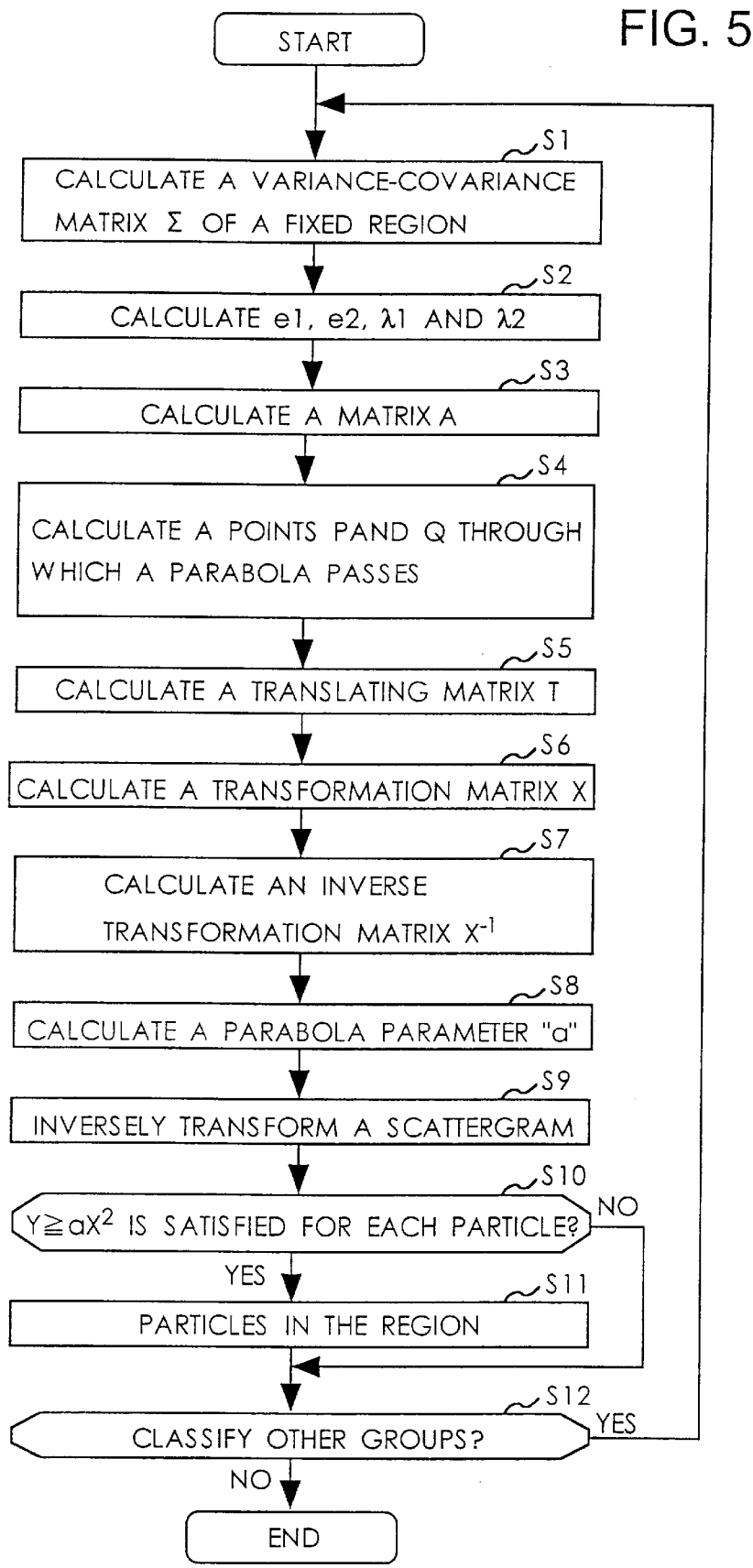
FIG. 5 is a flow chart showing a classifying procedure according to the embodiment of the present invention.

Next, the classifying section 2c carries out a classifying processing for the scattergram based on a flow chart shown in FIG. 5. First of all, a variance-covariance matrix Σ of particles in the fixed region R1 is obtained at Step S1. The variance-covariance matrix is defined in the following manner:

$$\sum = \begin{pmatrix} s_x^2 & s_{xy} \\ s_{xy} & s_y^2 \end{pmatrix}$$

wherein $s_x^2$ represents a variance in an x-axis direction of the particles in the fixed region R1, $s_y^2$ represents a variance in a y-axis direction of the particles in the fixed region R1, and $s_{xy}$ represents a covariance of the particles in the fixed region R1. $s_x^2$, $s_y^2$ and $s_{xy}$ are defined by the following equations.

$$s_x^1 = \frac{1}{N-1}\sum_{i=1}^{N}(x_i - x_m)^2 = \frac{1}{N-1}\left(\sum_{i=1}^{N} x_i^2 - Nx_m^2\right),$$

$$s_y^2 = \frac{1}{N-1}\sum_{i=1}^{N}(y_i - y_m)^2 = \frac{1}{N-1}\left(\sum_{i=1}^{N} y_i^2 - Ny_m^2\right),$$

$$s_{xy} = \frac{1}{N-1}\sum_{i=1}^{N}(x_i - x_m)(y_i - y_m) = \frac{1}{N-1}\left(\sum_{i=1}^{N} x_i y_i - Nx_m y_m\right),$$

$$x_m = \frac{1}{N}\sum_{i=1}^{N} x_i, \qquad y_m = \frac{1}{N}\sum_{i=1}^{N} y_i$$

Where N represents the total number of particles in the fixed region R1. Moreover, $x_i$ represents an x-coordinate of a particle i (i=1, 2, ..., N) in the fixed region R1 and $y_i$ represents a y-coordinate of the particle i (i=1, 2, ..., N) in the fixed region R1.

Next, an eigenvalue and a eigenvector of the variance-covariance matrix $\Sigma$ are calculated.

$\Sigma e = \lambda e$ $\lambda$=an eigenvalue of $\Sigma$
e=an eigenvector of $\Sigma$ The following equations are solved to obtain solutions $\lambda_1$ and $\lambda_2$.

$$\begin{vmatrix} s_x^2 - \lambda & s_{xy} \\ s_{xy} & s_y^2 - \lambda \end{vmatrix} = 0$$

Figure 6:
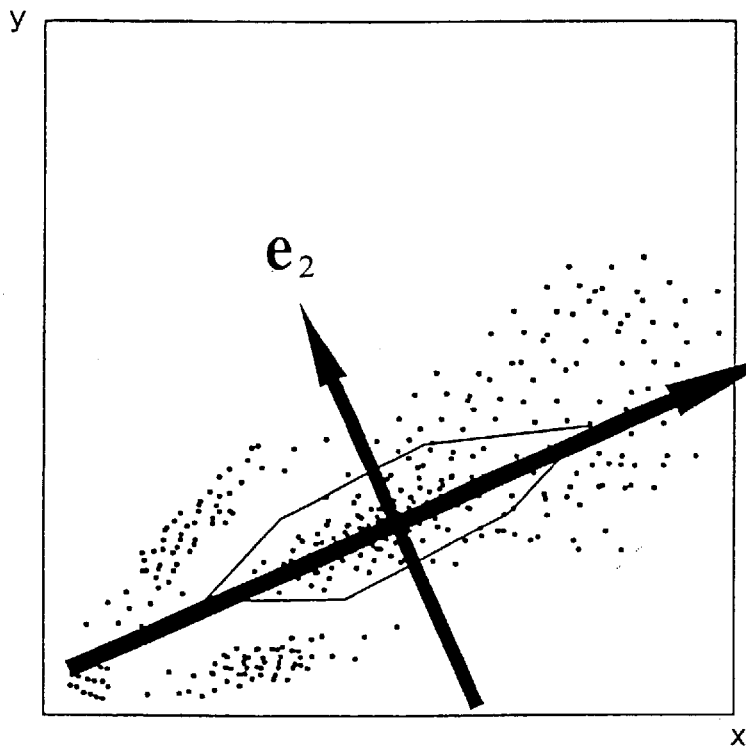
FIG. 6 is a chart showing the classifying method according to the embodiment of the present invention.

Then, eigenvectors corresponding to $\lambda_1$ and $\lambda_2$ are obtained respectively and e1 and e2 are obtained by normalizing the eigenvectors into a length 1. When $\lambda_1$ is greater than $\lambda_2$, the eigenvector e1 corresponding to $\lambda_1$ indicates a maximum variance direction of the particles in the fixed region R1 as shown in FIG. 6 and $\lambda_1$ indicates a variance in that direction. An inclination of a parabola which will be described below is obtained in that direction. Moreover, the eigenvector e2 corresponding to $\lambda_2$ indicates a direction orthogonal to e1 and $\lambda_2$ indicates a variance in that direction. $\lambda_2$ is set to a parameter of a degree of spread of the parabola. Thus, e1, e2, $\lambda_1$ and $\lambda_2$ are calculated at Step S2.

Figure 4:
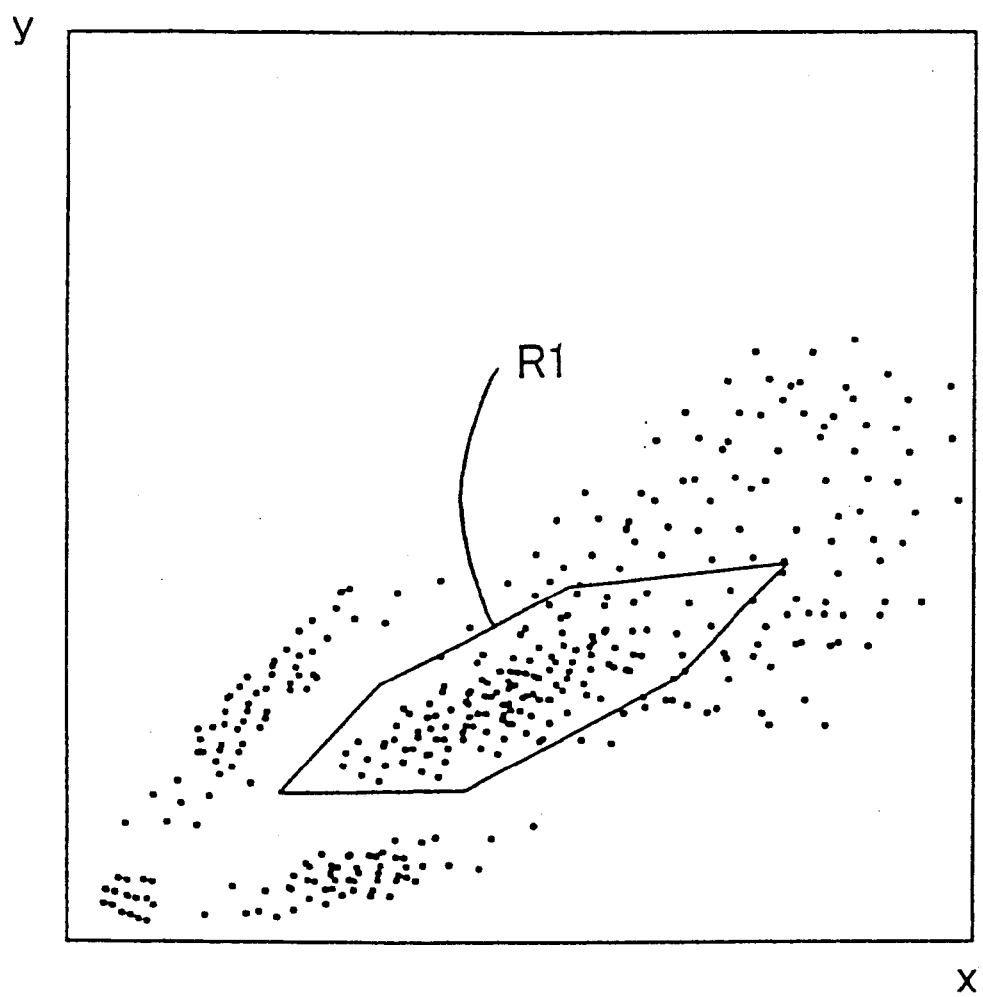
FIG. 4 is a chart showing a classifying method according to the embodiment of the present invention.
Figure 7:
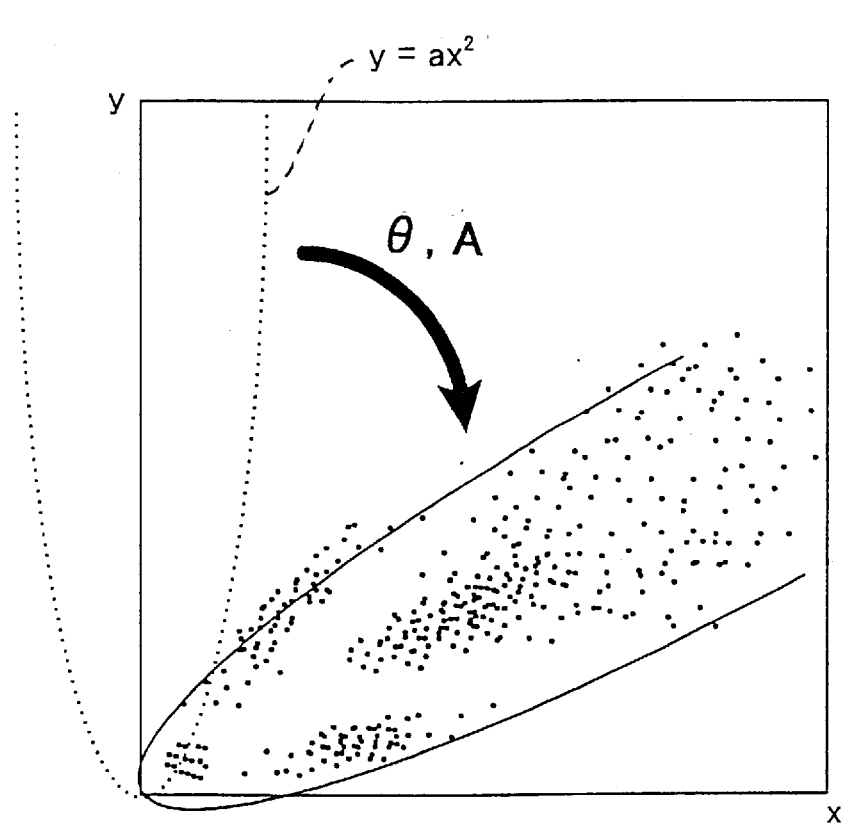
FIG. 7 is a chart showing the classifying method according to the embodiment of the present invention.

In the present embodiment, the parabola is calculated from the inclination direction e1 and the degree $\lambda_2$ of spread of the parabola which are obtained at the Step S2 and is used for a classifying parabola to classify a immature granulocyte (IMI) region of the scattergram shown in FIG. 4. The classifying parabola is obtained by rotating $y=ax^2$ clockwise by an angle $\theta$ by a matrix A as shown in FIG. 7 and translating the same by a vector T ($t_x$, $t_y$) shown in an arrow of FIG. 8. The matrix A is also calculated at Step S3.

Figure 13:
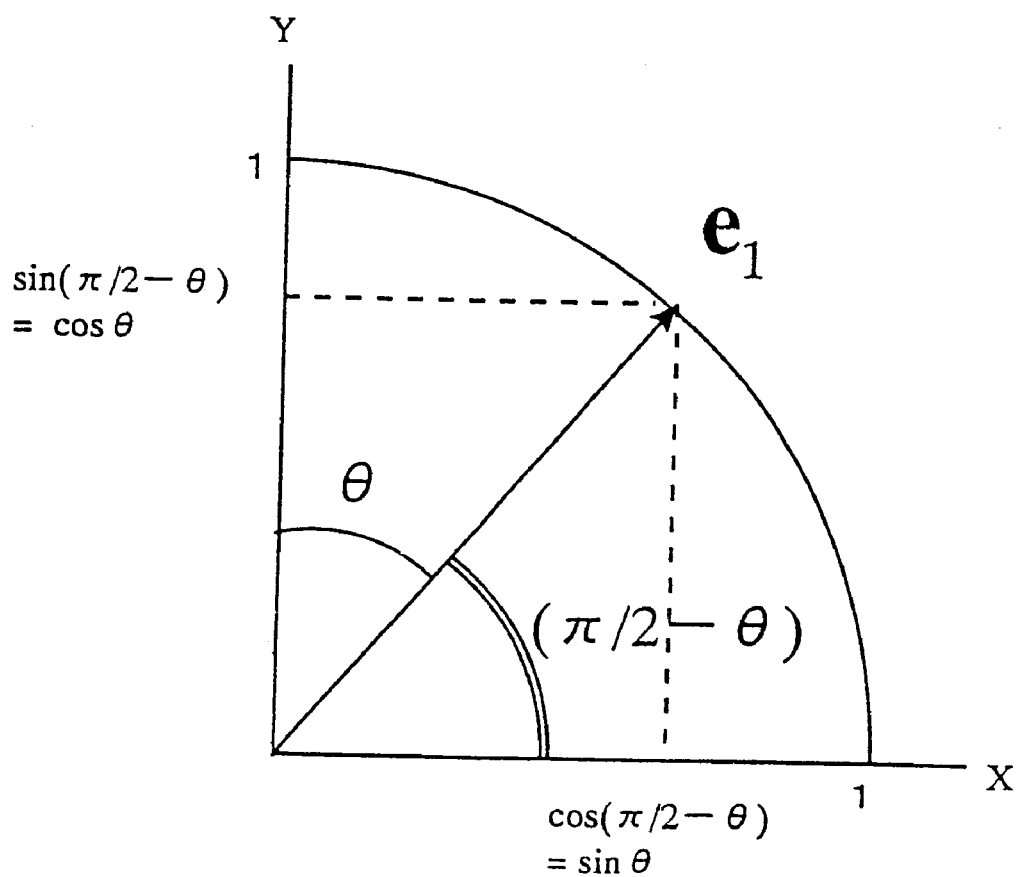
FIG. 13 is a chart illustrating a characteristic vector of a variance and covariance matrix according to the embodiment.

For the calculation of the matrix A, the angle $\theta$ representing the inclination of the parabola is obtained from e1. Since e1 is a unit vector, the following equation is obtained from FIG. 13.

$$e_1 = \left(\cos\left(\frac{\pi}{2} - \theta\right), \sin\left(\frac{\pi}{2} - \theta\right)\right)^t = (\sin\theta, \cos\theta)^t$$

Moreover, the matrix A is defined as follows.

$$A = \begin{pmatrix} \cos\theta & \sin\theta & 0 \\ -\sin\theta & \cos\theta & 0 \\ 0 & 0 & 1 \end{pmatrix}$$

Based on these equations, the matrix A is calculated.

Figure 8:
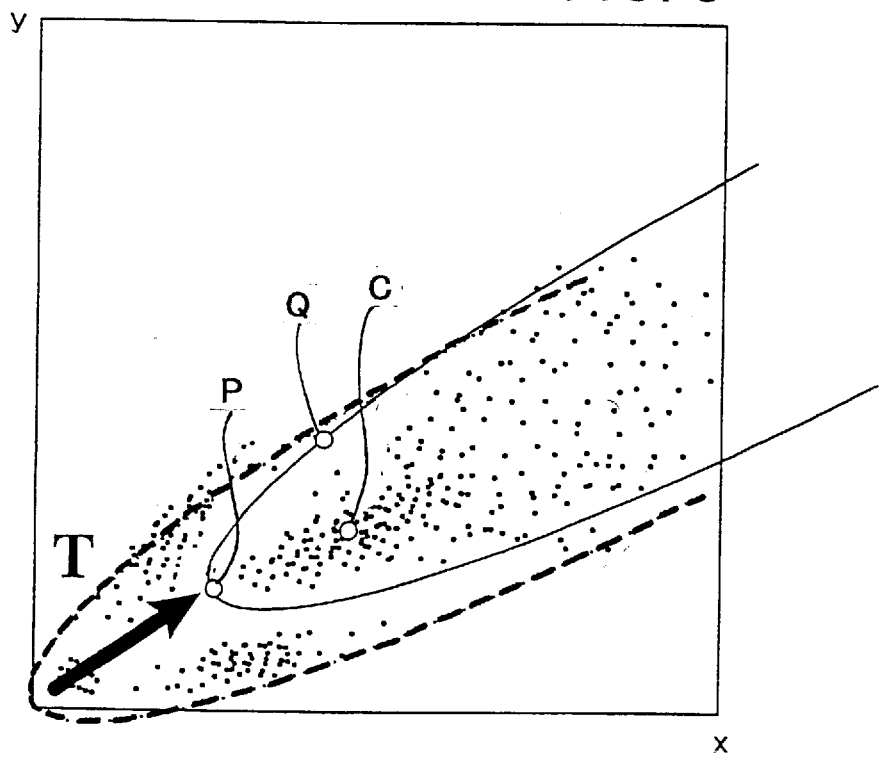
FIG. 8 is a chart showing the classifying method according to the embodiment of the present invention.
Figure 9:
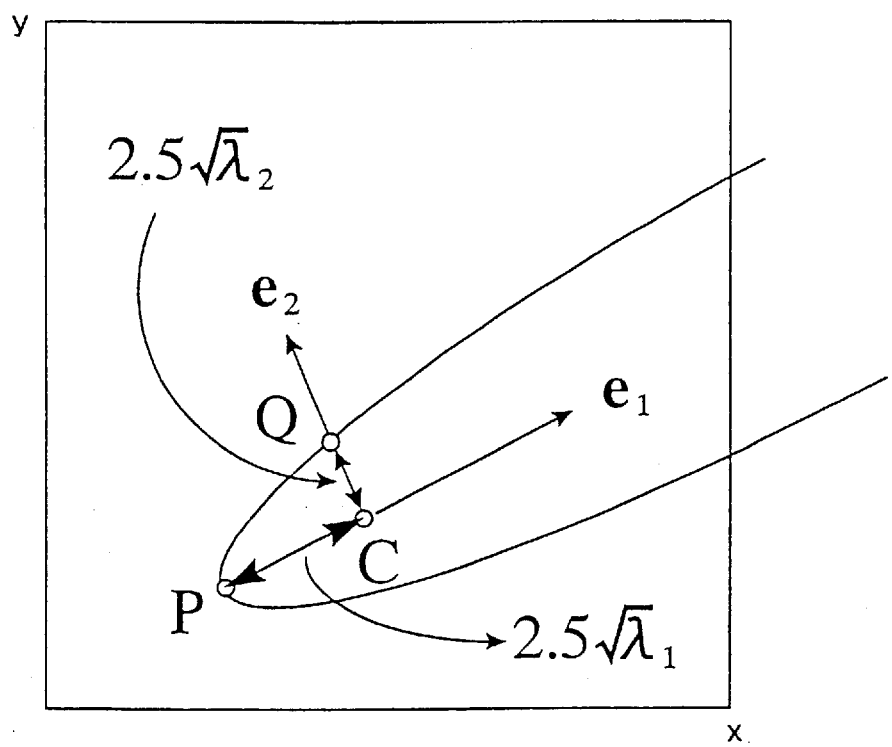
FIG. 9 is a chart showing the classifying method according to the embodiment of the present invention.

At Step S4, next, two points P and Q through which the classifying parabola passes are calculated based on a position C of a MFV (most frequency value) of the fixed region R1. If the point P is obtained by translating the origin by T ($t_x$, $t_y$) as shown in FIG. 8 and the point P=($t_x$, $t_y$)$^t$ is set, and the point P is set in a position obtained by movement from the MFV position C=($x_c$, $y_c$)$^t$ of the fixed region R1 toward the origin in the maximum variance direction by 2.5SD= $2.5\lambda_1^{1/2}$ as shown in FIG. 9 (SD=standard deviation), the following equation is obtained.

$$P = \begin{pmatrix} t_x \\ t_y \end{pmatrix} = C - 2.5\sqrt{\lambda_1}\, e_1 = \begin{pmatrix} x_c - 2.5\sqrt{\lambda_1}\sin\theta \\ y_c - 2.5\sqrt{\lambda_1}\cos\theta \end{pmatrix}$$

$$\therefore \begin{cases} t_x = x_c - 2.5\sqrt{\lambda_1}\sin\theta \\ t_y = y_c - 2.5\sqrt{\lambda_1}\cos\theta \end{cases}$$

On the other hand, it is assumed that a straight line extending in the e2 direction through the MFV position C=($x_c$, $y_c$)$^t$ in the fixed region R1 crosses the classifying parabola at the point Q. If the position of the point Q is determined in addition to the point P, the classifying parabola is defined. The point Q serves to determine the degree of spread of the classifying parabola. As described above, $\lambda_2$ is the parameter of the degree of spread of the parabola and is used for calculating the point Q. Here, it is assumed that the point Q passes through a position ($x_q$, $y_q$)$^t$ obtained by moving the position C in the e2 direction by $2.5SD=2.5\lambda_2^{1/2}$. If e2=($x_{e2}$, $y_{e2}$)$^t$ is set, the point Q can be calculated in the following manner.

$$Q = \begin{pmatrix} x_q \\ y_q \end{pmatrix} = C + 2.5\sqrt{\lambda_2}\, e_2 = \begin{pmatrix} x_c + 2.5\sqrt{\lambda_2}\, x_{e2} \\ y_c + 2.5\sqrt{\lambda_2}\, y_{e2} \end{pmatrix}$$

Consequently, the points P and Q are calculated so that the classifying parabola is determined. In addition, a matrix T (of which vector is shown in the arrow of FIG. 8) for by translating the parabola by ($t_x$, $t_y$) is calculated (Step S5).

Figure 10:
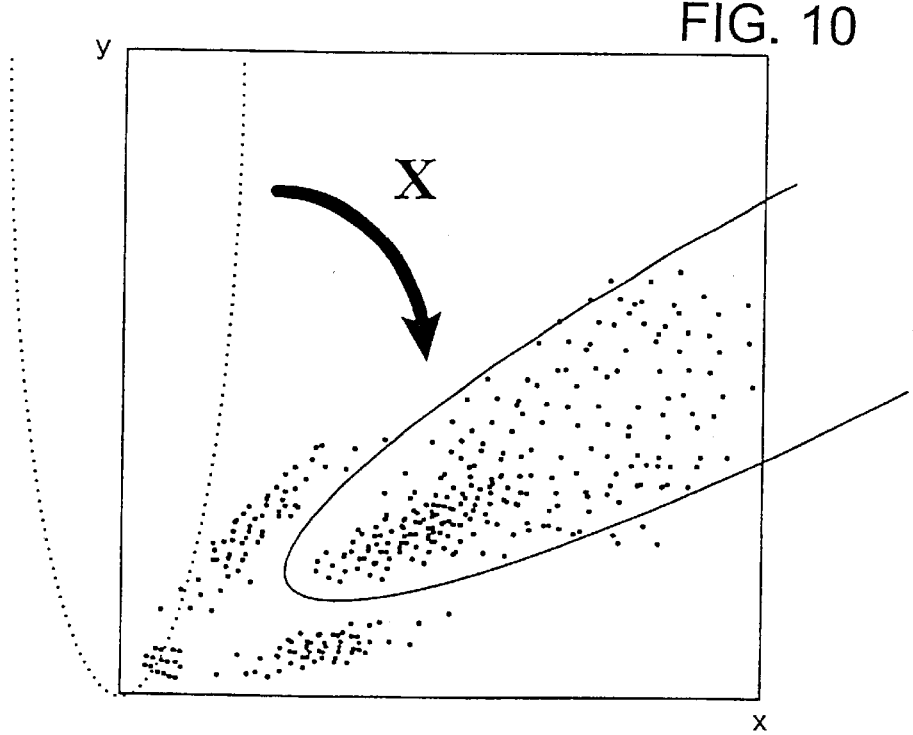
FIG. 10 is a chart showing the classifying method according to the embodiment of the present invention.

Based on the matrix A for rotating and inclining the parabola of $y=ax^2$ and the matrix T for translating the inclined parabola as described above, a transformation matrix X for rotating and translating the parabola $y=ax^2$ is obtained as shown in FIG. 10 (Step S6). The matrix X is as follows.

$$X = TA = \begin{pmatrix} 1 & 0 & t_x \\ 0 & 1 & t_y \\ 0 & 0 & 1 \end{pmatrix} \begin{pmatrix} \cos\theta & \sin\theta & 0 \\ -\sin\theta & \cos\theta & 0 \\ 0 & 0 & 1 \end{pmatrix} = \begin{pmatrix} \cos\theta & \sin\theta & t_x \\ -\sin\theta & \cos\theta & t_x \\ 0 & 0 & 1 \end{pmatrix}$$

Figure 11:
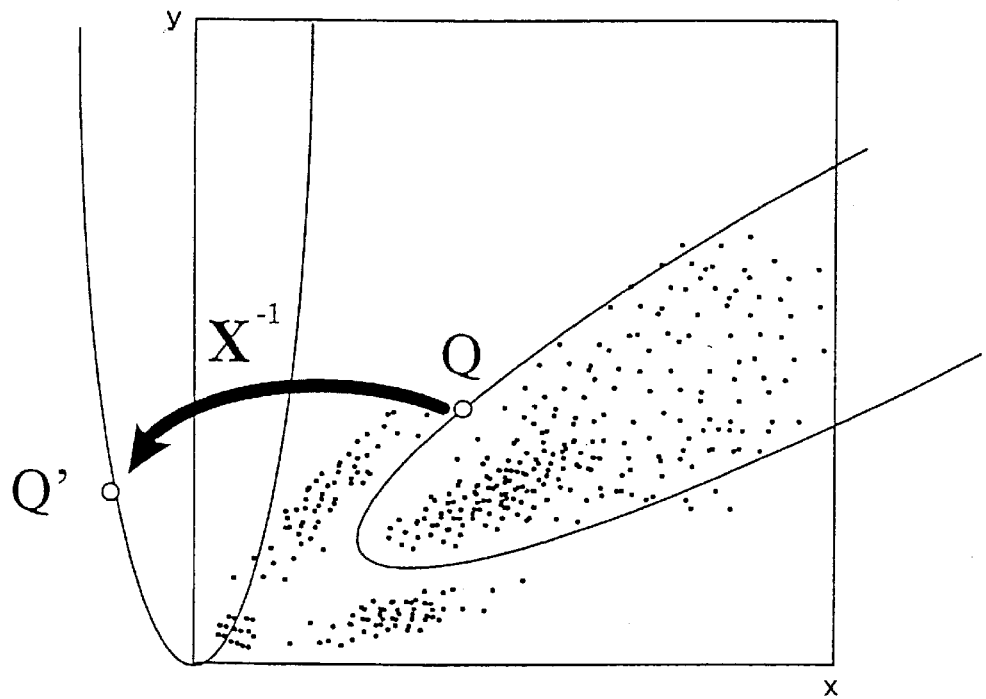
FIG. 11 is a chart showing the classifying method according to the embodiment of the present invention.

The following is apparent from the matrix X. As shown in FIG. 10, the classifying parabola is obtained by projecting $y=ax^2$ with the matrix X. Consequently, if the scattergram is inversely transformed by using an inverse matrix $X^{-1}$ of the matrix X to project the particles on the scattergram as shown in FIG. 11, all the particles included inside $y=ax^2$ are particles to be classified. Therefore, the inverse matrix $X^{-1}$ of the matrix X is calculated in the following manner at Step S7.

$$X^{-1} = (TA)^{-1} = A^{-1}T^{-1}$$

$$= \begin{pmatrix} \cos\theta & -\sin\theta & 0 \\ \sin\theta & \cos\theta & 0 \\ 0 & 0 & 1 \end{pmatrix} \begin{pmatrix} 1 & 0 & -t_x \\ 0 & 1 & -t_y \\ 0 & 0 & 1 \end{pmatrix}$$

$$= \begin{pmatrix} \cos\theta & -\sin\theta & t_x\cos\theta + t_y\sin\theta \\ \sin\theta & \cos\theta & -t_x\sin\theta - t_y\cos\theta \\ 0 & 0 & 1 \end{pmatrix}$$

Figure 12:
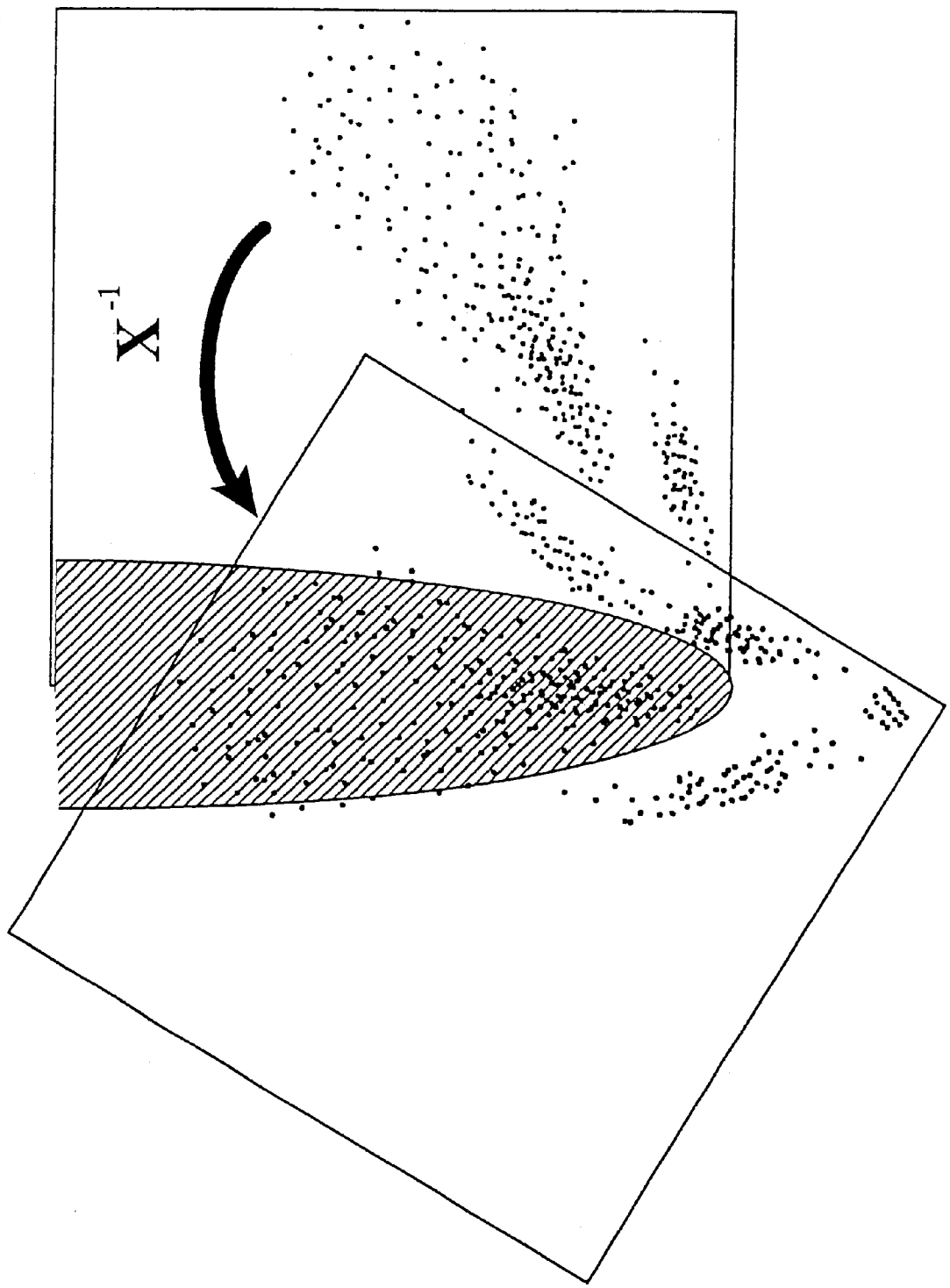
FIG. 12 is a chart showing the classifying method according to the embodiment of the present invention.

At Step S8, next, a coefficient "a" which is a parameter for determining the parabola of $y=ax^2$ is calculated. The fact that the parabola passes through the position obtained by moving the MFV position $C=(x_c, y_c)^t$ in the fixed region R1 in the e2 direction by $2.5SD=2.5\lambda_2^{1/2}$, that is, the parabola passes through the point $Q=(x_q, y_q)^t$ as shown in FIG. 9 is utilized. As shown in FIG. 12, if a position obtained by transforming the point Q with the matrix $X^{-1}$ is set to $Q'=(x'_q, y'_q)^t$, Q' satisfies the parabola of $y=ax^2$ so that "a" is obtained in the following manner.

$$y'_q = ax'_q$$

$$\therefore a = \frac{y'_q}{x'_q}$$

If the particles on the scattergram are projected by inversely transforming the scattergram using the inverse matrix $X^{-1}$, all the particles included inside $y=ax^2$ are particles to be classified as described above. The inverse transformation is carried out at Step S9. If an optional point on the scattergram is set to $p(x, y)$ and a point projected by the matrix $X^{-1}$ is set to $p'(x', y')$, the following calculation can be carried out.

$$\begin{pmatrix} x' \\ y' \\ 1 \end{pmatrix} = X^{-1} \begin{pmatrix} x \\ y \\ 1 \end{pmatrix}$$

$$= \begin{pmatrix} \cos\theta & -\sin\theta & t_x\cos\theta + t_y\sin\theta \\ \sin\theta & \cos\theta & -t_x\sin\theta - t_y\cos\theta \\ 0 & 0 & 1 \end{pmatrix} \begin{pmatrix} x \\ y \\ 1 \end{pmatrix}$$

$$= \begin{pmatrix} \cos\theta \cdot x - \sin\theta \cdot y + t_x\cos\theta + t_y\sin\theta \\ \sin\theta \cdot x + \cos\theta \cdot y - t_x\sin\theta - t_y\cos\theta \\ 1 \end{pmatrix}$$

whether the point $p'(x', y')$ which is a result of the inverse transformation at the Step S9 is present outside or inside a region to be classified as an IMI region is decided by the following equation.

$$y' = ax'^2$$

If $y' < ax'^2$ is satisfied, $p(x, y)$ is present outside the IMI region.

If $y' \geq ax'^2$ is satisfied, $p(x, y)$ is present inside the IMI region.

In order to use the equation, it is necessary to determine "a" representing the degree of spread of the parabola, which is calculated at the Step S8.

At Step S10, the decision is carried out for each particle on the scattergram by using the above-mentioned equation. If $y \geq ax^2$ is satisfied, the particle is regarded to be distributed in the IMI region (Step S11).

As described above, the classification can be carried out with the parabola of $y=ax^2$. In the case in which another cluster is to be classified (Step S12), a fixed region is appropriately set on the scattergram corresponding to the type of the particle to be classified and the Steps S1 to S11 are repeated. When the classifying processing is completed, the control section 2d counts the number of the particles in each classifying region and causes the output section 3 to output a result of the counting operation.

According to the present invention, a particle group which is not normally distributed in all directions in the scattergram, for example, a particle group of which distribution does not concentrate in the vicinity of the center of gravity but is extended in a specific direction can also be classified accurately. Moreover, the classifying line is calculated based on the distribution state of the particles in a predetermined particle distribution region. Therefore, it is also possible to carry out an accurate classification corresponding to a fluctuation in an inclination of the cluster.

What is claimed is:

1. A particle analyzer comprising:
    a detecting section for detecting at least two kinds of parameters from a plurality of particles included in a sample, the two kinds of parameters representing characteristics of each particle,
    a processing section for processing the parameters detected by the detecting section; and
    an output section for outputting a result processed by the processing section,
    wherein the processing section includes
        a distribution chart creating section for creating a scattergram of the particles based on the detected parameters,
        a region setting section for presetting a particle distribution region in the created scattergram, and
        a classifying section for calculating a classifying line corresponding to a particle distribution state in the preset particle distribution region and for classifying the particles on the scattergram by the calculated classifying line.

2. The particle analyzer of claim 1, wherein the classifying section obtains a variance-covariance matrix $\Sigma$ of the particles distributed in the set particle distribution region and an eigenvector of $\Sigma$ and an eigenvalue of $\Sigma$, and calculates the classifying line from the eigenvector and eigenvalue of $\Sigma$.

3. The particle analyzer of claim 1, wherein the classifying line is a parabola.

4. The particle analyzer of claim 2, wherein the classifying line is a parabola and the classifying section obtains an inclination of the parabola from the eigenvector of $\Sigma$ and a degree of spread of the parabola from the eigenvalue of $\Sigma$, thereby calculating the parabola.

5. The particle analyzer of claim 3, wherein when the scattergram is represented on X-Y orthogonal coordinates, the classifying section carries out the steps of;
    inclining a parabola represented as $y=ax^2 (a>0)$ in a maximum variance direction of the particles in the set particle distribution region,
    translating the parabola on the coordinates so that a point of a minimum value of $y=ax^2$ is coincident with a point positioned apart in the maximum variance direction by n times as great as a standerd deviation from a point of a most frequency value of the particles in the set particle distribution region and the parabola passes through a point positioned apart in a direction orthogonal to the maximum variance direction by n times as great as a standerd deviation from the point of the most frequency value, and determining the inclined and translated parabola as the classifying line.

6. The particle analyzer of claim 5, wherein the classifying section further has a function of carrying out coordinate transformation of the scattergram such that the classifying line is $y=ax^2$.

7. A particle classifying method which is carried out by the analyzer of claim 1, the method comprising the steps of:

detecting at least two kinds of parameters from a plurality of particles included in a sample, the two kinds of parameters representing characteristics of each particle;

creating a scattergram based on the detected parameters;

obtaining a variance-covariance matrix $\Sigma$ of the particles distributed in a predetermined particle distribution region in the scattergram and an eigenvector of $\Sigma$ and an eigenvalue of $\Sigma$;

calculating a classifying line from the eigenvector and eigenvalue of $\Sigma$; and classifying the particles on the scattergram by the calculated classifying line.

8. The particle classifying method of claim 7, wherein the classifying line is a parabola and the parabola is calculated from an inclination of the parabola obtained from the eigenvector of $\Sigma$ and a degree of spread of the parabola obtained from the eigenvalue of $\Sigma$.

9. A particle analyzer comprising:

a detecting section for detecting at least two kinds of parameters from a plurality of particles included in a sample, the two kinds of parameters representing characteristics of each particle, a processing section for processing the parameters detected by the detecting section; and an output section for outputting a result processed by the processing section, wherein the processing section includes a distribution chart creating section for creating a scattergram of the particles based on the detected parameters, a region setting section for presetting a particle distribution region in the created scattergram, and a classifying section for calculating a parabola corresponding to a particle distribution state in the preset particle distribution region and for classifying the particles on the scattergram by the calculated parabola.

10. A particle classifying method which is carried out by the analyzer of claim 9, the method comprising the steps of:

detecting at least two kinds of parameters from a plurality of particles included in a sample, the two kinds of parameters representing characteristics of each particle;

creating a scattergram based on the detected parameters;

obtaining a variance-covariance matrix $\Sigma$ of the particles distributed in a predetermined particle distribution region in the scattergram and an eigenvector of $\Sigma$ and an eigenvalue of $\Sigma$;

calculating a parabola from the eigenvector and eigenvalue of $\Sigma$; and classifying the particles on the scattergram by the calculated parabola.

* * * * *